United States Patent
Patashnick et al.

(10) Patent No.: US 6,502,450 B1
(45) Date of Patent: **\*Jan. 7, 2003**

(54) SINGLE DETECTOR DIFFERENTIAL PARTICULATE MASS MONITOR WITH INTRINSIC CORRECTION FOR VOLATILIZATION LOSSES

(75) Inventors: Harvey Patashnick, Voorheesville, NY (US); Georg Rupprecht, Voorheesville, NY (US)

(73) Assignee: Rupprecht & Patashnik Company, Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,518

(22) Filed: May 8, 2000

Related U.S. Application Data

(60) Provisional application No. 60/133,320, filed on May 10, 1999.

(51) Int. Cl.$^7$ .................................................. G01F 1/76
(52) U.S. Cl. ........................ 73/23.21; 73/28.04; 73/861; 702/100
(58) Field of Search ............................ 73/23.21, 23.28, 73/28.01, 28.02, 28.04, 28.05, 28.06, 1.06, 1.34, 1.31, 861–861.03, 32 R, 32 A, 433, 434, 865; 702/24, 80, 100, 101, 129, 173

(56) References Cited

U.S. PATENT DOCUMENTS

| | | | | |
|---|---|---|---|---|
| 3,926,271 A | | 12/1975 | Patashnick | 177/210 FP |
| 4,003,240 A | * | 1/1977 | Durbin | 73/1.06 X |
| 4,391,338 A | | 7/1983 | Patashnick | 177/210 FP |
| 4,525,627 A | | 6/1985 | Krempl et al. | 250/345 |
| 4,827,760 A | | 5/1989 | Saito | 73/864.71 X |
| 4,960,992 A | * | 10/1990 | Vestal et al. | 73/864.81 X |
| 5,027,642 A | | 7/1991 | Wen et al. | 73/73.2 |
| 5,049,317 A | * | 9/1991 | Kiske et al. | 73/1.31 X |
| 5,157,340 A | | 10/1992 | Walton et al. | 324/641 |
| 5,255,555 A | | 10/1993 | McKeiqu | 73/28.01 |
| 5,279,146 A | | 1/1994 | Asano et al. | 73/28.04 |
| 5,279,970 A | | 1/1994 | Patashnick et al. | 436/133 |
| 5,349,844 A | | 9/1994 | Lilienfeld | 73/28.01 |
| 5,369,981 A | | 12/1994 | Merz et al. | 73/28.01 |
| 5,526,110 A | * | 6/1996 | Braymen | 350/316 |
| 5,571,945 A | | 11/1996 | Koutrakis et al. | 73/28.03 |
| 5,661,225 A | * | 8/1997 | Ridgeway et al. | 73/1.06 |
| 5,665,902 A | | 9/1997 | Wang et al. | 73/28.01 |
| 5,763,360 A | * | 6/1998 | Gundel et al. | 502/402 |
| 5,880,355 A | | 3/1999 | Park et al. | 73/28.01 |
| 5,932,795 A | | 8/1999 | Koutrakis et al. | 73/28.01 |
| 5,970,781 A | | 10/1999 | Hiss et al. | 73/28.01 |
| 6,016,688 A | | 1/2000 | Hiss et al. | 73/28.01 |
| 6,151,953 A | * | 11/2000 | Patashnick et al. | 73/28.01 |
| 6,205,842 B1 | | 3/2001 | Patashnick et al. | 73/28.01 |

FOREIGN PATENT DOCUMENTS

| | | | | |
|---|---|---|---|---|
| EP | 0 779 510 A2 | 6/1997 | | G01N/27/00 |
| GB | 2 227 316 A | 7/1990 | | G01N/15/06 |

* cited by examiner

Primary Examiner—Thomas P. Noland
(74) Attorney, Agent, or Firm—Heslin Rothenberg Farley & Mesiti P.C.

(57) ABSTRACT

The mass of particulate matter in a particle laden gas stream is measured using a single mass detector. The particle laden gas stream and a substantially identical but particle-free gas stream alternately engage the mass detector during successive measurement time periods. A difference between a reading provided by the mass detector for a current measurement time period and a reading provided by the mass detector for a consecutive measurement time period is determined. This difference intrinsically corrects for volatilization losses occurring during the current measurement time period. A measure of the mass or concentration of particulate matter in the particulate laden gas stream is determined from this difference.

18 Claims, 3 Drawing Sheets

SINGLE DETECTOR DIFFERENTIAL PARTICULATE MASS MONITOR WITH INTRINSIC CORRECTION FOR VOLATILIZATION LOSSES

This application claims the benefit under 35 U.S.C. 119(e) of U.S. provisional application 60/133,320 filed May 10, 1999.

TECHNICAL FIELD

This invention relates, in general, to the measurement of particulate matter suspended in a fluid medium and, more specifically, to measurement of the mass and/or concentration of particulate matter suspended in ambient air or in other gaseous environments, e.g. in diesel exhaust, or in mines, smoke stacks, industrial facilities, etc. Particulate matter is the general term which refers to condensed solid, semi-solid, or liquid material produced as a result of natural or man-made processes, and which due to small size, is capable of being suspended in the air or other fluid medium.

BACKGROUND ART

The measurement of particulate matter in ambient air is important for a variety of reasons, the most important of which is related to health effects. Suspended particulate matter is known to produce a variety of deleterious health effects when inhaled. As a result, regulatory agencies around the world require monitoring of the levels of particulate matter. The levels are measured in terms of concentration, i.e. micrograms of particulate matter per cubic meter of air. Reference techniques for this measurement are presently defined in terms of a mass measurement utilizing a filter medium to capture the particulate matter and the total volume of air which has been filtered by the medium over a given period of time. There are various means available to unambiguously determine the flow rate through the filter over time (and hence the volume of air sampled), but surprisingly the mass measurement is not straightforward due to the complex nature of ambient particulate matter which results in unstable mass deposition on the filter.

This problem involving the measurement of particulate matter in ambient air is well-known. The uncertainty arises since the particulate mass used as a basis for mass concentration computations is defined as the mass captured on the filter media which is not necessarily the mass of the particles as they exist in the ambient air. Unlike measurements of major criteria gaseous pollutants, what is defined as particulate matter can change its mass as a result of loss or gain of volatile substances associated with the particulate matter and filter media. While gaseous pollutants exist as definable molecular species ($SO_2$, $O_3$, CO, etc.), particulate matter can be a combination of different substances with different volatilization rates, reactive, desorptive, absorptive, and adsorptive properties. In addition, the mass of particulate matter on the filter can be affected by the filter material itself, the particulate matter already collected on the filter, the face velocity through and pressure drop across the filter, as well as by the humidity, temperature and composition of the gas stream passing through the collection medium.

Both direct and indirect measurement techniques have been employed in an effort to quantify particulate matter mass. Each method which has been developed to date, however, has limitations in obtaining a measurement of the actual mass of particulate matter as it exists in its suspended form. Direct mass measurements as represented by weighing material captured on a substrate such as a filter are susceptible to instrument effects due, for example, to temperature or pressure changes, and to volatile component losses which are not easily quantifiable. Indirect methods such as light scattering measurements on the other hand are inherently inaccurate as there is no physical connection between other properties of particles and particle mass.

To compensate for instrument effects in direct mass measurements, a differential particulate mass measurement microbalance employing a pair of oscillating quartz crystal detectors has previously been proposed. In this earlier approach, a particle laden gas stream impacts upon the first detector and a particle free gas stream impacts the second detector. The second mass detector is used as a reference to cancel out detector instrument effects from a mass reading provided by the first detector. U.S. Pat. No. 5,571,945 discloses a similar measurement approach employing a pressure sensor to measure a pressure differential between a pair of particulate matter collectors; U.S. Pat. No. 5,349,844 discloses a similar approach for use with a filter that is caused to oscillate in a direction substantially perpendicular to a plane of the filter. However, volatilization losses are not accounted for in these earlier systems.

As a result of the above described difficulties, the current reference method in the United States is a method dependent technique which does not necessarily represent an accurate measure of particulate mass as it actually exists in its undisturbed state in the air. The reference method consists of filter equilibration under a defined range of temperature and humidity conditions, a pre-collection weighing of the filter, the installation of the filter in a manual sampler, the sampling of ambient air (for a 24-hour period), the removal of the filter from the sampling device, a post-collection conditioning under the same equilibration conditions as before, and finally a post-collection weighing. This methodology is intended to provide a consistent set of measurements between identical samples.

However, for the reasons stated above, results based on this method do not represent measurements to which an accuracy can be assigned, even loosely, i.e. to what accuracy is the particulate mass as it exists in the atmosphere measured by the mass determined from the filter? This is a serious problem, and one has to accept the fact that these measurements are only an indication of particulate levels. As a result, the current reference method represents simply a standardized procedure, and not a scientifically-based measurement standard for airborne particulate matter.

Volatile components are a confounding influence on these measurements. While the filter resides in the sampling hardware, important factors that influence the reactions taking place on the filter substrate, such as temperature and humidity, vary in an ill-defined manner. During sampling, the mass on and of the filter can increase dramatically during periods of decreasing temperature and increasing relative humidity (nighttime), and may experience substantial loss of semi-volatile materials when the temperature increases and humidity decreases (daytime). These same type of effects can be associated with air mass changes, and other meteorological events. Further, the collection filter may be exposed to widely varying hot or cold temperatures once sampling is complete and before it is removed from the sampler as well as during transportation to a laboratory for conditioning and weighing.

Not only does the mass of collected particulate matter and the filter change depending upon the conditions to which they are exposed, but the air stream through the filter creates a pressure differential across the filter which tends to strip off volatile components of the particulate matter. In effect, the interaction of the particles with the filter tends to modify the nature of the particulate matter as soon as it is collected, thereby affecting the accuracy of the desired measurement of the particulate matter as it is suspended in ambient air. As health concerns heighten, and measurement instrumentation becomes more sensitive, there is a trend towards measurement of even finer particulate matter, e.g. particles of 2.5 microns or less. With smaller particles, the impact of volatilization losses upon the mass measurement readings becomes even more pronounced.

A compelling need thus exists for a measurement instrument that can accurately measure the mass or concentration of particulate matter suspended in ambient air or other gaseous environments.

SUMMARY OF THE INVENTION

The present invention provides a method and apparatus which overcomes the problems described above and provides a collection-based direct mass measurement that allows the accurate quantification of the mass of ambient air or other gas borne particulate matter including volatile components thereof. The measurement approach of the present invention not only cancels out detector instrument effects but also intrinsically corrects for volatilization losses. For purposes of this disclosure, the term "volatilization losses" is used broadly to include vaporization, absorption, adsorption, desorption, reactive and other effects which influence (positively or negatively) the mass of collected particulate matter. Some of the effects are generally known as collector (e.g. filter) artifacts.

In accordance with the principles of the present invention, apparatus for measuring the mass of particulate matter in a particle laden gas stream includes a mass detector, and first means for providing a particle free gas stream otherwise substantially identical to the particle laden gas stream. Switching means causes said particle laden gas stream and said particle free gas stream to alternately engage said mass detector during successive measurement time periods. A difference between a reading provided by the mass detector for a current measurement time period and a reading provided by the mass detector for a consecutive measurement time period is computed. This difference intrinsically corrects for volatilization losses occurring during the current measurement time period. A measure of the mass or concentration of particulate matter in the particle laden gas stream is determined from this difference.

Advantageously, the first means for providing a particle free gas stream comprises particle removal means for removing substantially all particulate matter from said particle laden gas stream. Optimally, said particle removal means removes the particulate matter from the particle laden gas stream without appreciably affecting gas stream temperature, pressure and flow rate. Such particle removal is preferably accomplished using an electrostatic precipitator. The precipitator preferably operates with a positive corona and low current.

The mass detector may comprise an oscillating element microbalance. The detector may comprise a hollow element oscillating in a clamped-free mode, with a filter supported at a free end of the element. The filter serves to collect particulate matter from the particle laden gas stream when this stream engages the detector. Fluid control means can advantageously maintain a substantially constant gas stream flow at the filter of the detector during each measurement period. In the oscillating element microbalance embodiment, mass readings provided by the mass detector are advantageously based upon detected change of frequency of oscillation of the oscillating element with respect to time.

In another aspect of the invention, the switching means of the mass measuring apparatus causes: (a) the particle laden gas stream to engage the mass detector during each of odd numbered ones of the successive measurement time periods, and (b) said particle free gas stream to engage the mass detector during each of even numbered ones of the successive measurement time periods. When the detector is engaged by the particle laden gas stream, it measures mass gain; when the detector is engaged by the particle free gas stream, it measures mass lost due to volatilization of volatile components of the particulate matter. The measured mass lost is added to the measured mass gain to determine the measure of the mass of the particulate matter. Each successive measurement time period lasts for a short time, preferably fifteen minutes or less; about a minute or less being presently considered as most preferred.

In another aspect of the invention, the readings provided by the mass detector each comprise a mass rate reading, which limits accumulation of any calibration errors in the mass measurement.

In yet another aspect of the present invention, corrected mass concentration is computed from a corrected mass rate which combines mass rate readings from the mass detector for two successive measurement periods.

The present invention also presents a significant improvement to existing differential particle mass measurement systems. In such systems, a particle laden gas stream engages a first mass detector and a particle free gas stream engages a second mass detector. The second mass detector is used as a reference to cancel out detector instrument effects from a reading provided by the first mass detector. According to the present invention, a differential particle mass measurement system is improved by inclusion of switching means for causing the particle laden gas stream and the particle free gas stream to alternately engage a single mass detector, during successive measurement time periods. In this fashion, correction is intrinsically provided for volatilization losses occurring during the successive measurement time periods, calibration or matching of multiple detectors is avoided, and the complexity and cost of the measurement device is reduced.

In a further aspect of the present invention, apparatus for measuring the mass of particulate matter, including volatile components thereof, in a particle laden gas stream is provided. This apparatus includes a mass detector, means for directing the stream to continually engage the mass detector, and particle removal means for removing substantially all particulate matter from the stream when the particle removal means is activated. Control means activates the particle removal means for alternate successive measurement time periods. A difference is determined between a first reading provided by the mass detector and a second reading provided by the mass detector for successive measurement time periods. This difference intrinsically corrects for volatilization losses occurring during the measurement time periods. A measure of the mass or concentration of particulate matter in the particle laden gas stream is determined from this difference.

Pursuant to a still further aspect of the present invention, a differential particle mass measurement method is improved. In the known method, a particle laden gas stream engages a first mass detector. The first mass detector collects a current particle sample from the gas stream during a current measurement time period and measures mass gain due thereto. A second mass detector is used as a reference to cancel out detector instrument effects. The present invention improves upon this method by using a single mass detector to not only cancel out detector instrument effects but to also effectively measure a change in particle property occurring during said current measurement time period. This change in particle property usually comprises a loss of mass due to volatilization of collected volatile particles. The mass lost due to volatilization as measured by the mass detector is added to the mass gain measured by the mass detector to yield a corrected particle mass measurement for the current measurement time period. The measured loss of mass occurs during a consecutive measurement time period (i.e., during a period just before or after the current measurement time period) in an earlier collected particle sample; this earlier collected particle sample having been collected by the mass detector in a preceding measurement time period. Preferably, the current measurement time period and the consecutive measurement time period are of such short duration as to ensure substantially identical volatilization during said consecutive measurement time period of the earlier collected sample and the current particle sample.

The present invention provides numerous significant benefits and advantages. Foremost among these is its intrinsic correction for volatilization losses occurring during measurement time periods. Using short measurement time periods ensures that the particulate mass measurement includes an accurate representation of the volatile mass associated with the collected particulate under any selected temperature including varying ambient temperature conditions. Since the mass detector sees substantially identical collector (e.g. filter) and instrument artifacts during a pair of successive measurement time periods, compensation for instrument effects is effective and complete when the readings from one measurement time period are subtracted from those of the other. The preferred use of an electrostatic precipitator for particle removal prevents any pressure disturbance from occurring. The electrostatic precipitator also facilitates switching of the particle content of the gas stream on and off electrically and instantaneously with no mechanical motion being necessary. The switching of the gas stream also effectively expands collector (e.g. filter) life by a factor of 2 compared to a continuous particle collector system. Further, if two differential measurement instruments are run side-by-side in accordance with the principles of the present invention, one at ambient temperature and the other at a significantly elevated temperature, then a division between volatile and non-volatile components of the ambient particulate matter can be obtained. The use of a single detector provides additional cost and reliability benefits.

BRIEF DESCRIPTION OF THE DRAWINGS

These and other aspects, features and advantages of the present invention will be more readily understood from the following detailed description of preferred embodiments when read in conjunction with the accompanying drawing figures in which.

DETAILED DESCRIPTION

The goal of the present invention is to accurately measure the mass of particulate matter suspended in ambient air (or other gaseous environment) including volatile components thereof. This is accomplished by causing a particle laden gas stream and a substantially identical but particle free gas stream to alternately engage a mass detector during successive measurement time periods. With suitably short measurement time periods, taking a difference between successive readings provided by the mass detector, in effect adds to the measured mass gain of the collected particulate matter, the mass lost due to volatilization during the measurement time interval thereby providing an accurate measurement of total particulate mass in the gas stream.

Figure 1:
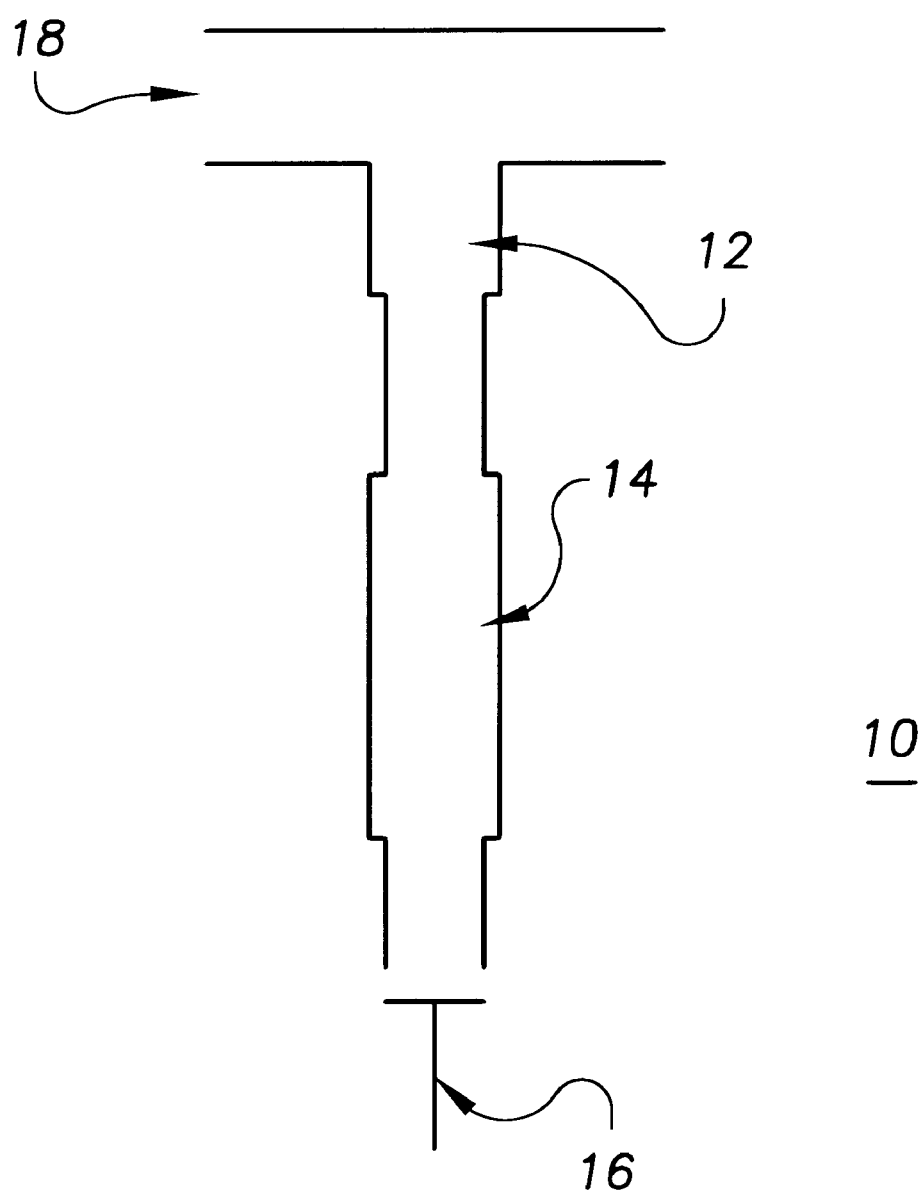
FIG. 1 is a simplified schematic illustration of one embodiment of a differential particulate mass measuring apparatus of the present invention.

A first embodiment of the particulate mass measurement instrument of the present invention is schematically illustrated in FIG. 1. The instrument 10 includes an inlet 12 in pneumatic communication with a selectively activatable particle remover 14 and a mass detector 16. A particle laden gas stream 18 enters the inlet 12, passes through the selectively activatable particle remover 14 and continually engages the mass detector 16. The term "engages" is used herein to broadly connote the interaction of a gas stream with a mass detector. Such interaction may take many different forms depending upon the nature of the mass detector employed.

Inlet 12 would normally include a separator for pre-separating out of the particle laden gas stream, particles larger than a predetermined "cut-off" size. Inlets with PM10 and/or PM2.5 separators, for example, are well known and commercially available.

The particle laden gas stream exiting inlet 12 is then channeled to and through selectively activatable particle remover 14. When activated, particle remover 14 removes substantially all particulate matter from the gas stream, without appreciably affecting gas stream temperature, pressure and flow rate. Such particle removal can be advantageously implemented using an electrostatic precipitator of the same general type as is commonly used in air cleaning equipment. In order to reduce ozone production, an electrostatic precipitator operating with a positive corona and very low current, e.g. on the order of tens to hundreds nanoamps, is preferred. The current should be sufficient to cause the precipitator to remove substantially all particulate matter from the gas stream.

Particle remover 14 is selectively activated during alternate successive measurement time periods to remove particulate matter from gas stream 18 during the alternate successive measurement time periods.

For example, for a first measurement time period, particle remover 14 may be turned on. During the next measurement time period, particle remover 14 is turned off. This alternating activation pattern continues for successive measurement time periods. Advantageously, each time period is of relatively short duration, preferably on the order of fifteen minutes or less, more preferably on the order of five minutes or less, and most preferably on the order of one minute or less.

The gas stream 18 emerging from the particle remover 14 continually engages mass detector 16 throughout the successive measurement time periods.

Although other direct mass or indirect mass detectors such as quartz crystal microbalances, beta absorption monitors, pressure drop monitors, etc. may also be used, the preferred implementation of mass detector 16 is a tapered hollow element oscillating microbalance. The latter instrument is preferred because of its high mass sensitivity, real-time capability, direct inertia-based mass measurement, and high collection efficiency utilizing filtration.

High mass sensitivity is important since the amount of mass which needs to be measured is in the microgram and sub-microgram range. Real-time measurement is important since mass volatilization can occur in short time frames. Direct mass measurement is desirable to avoid ambiguity in what is measured and also allows for a mass standard traceable calibration. Filtration ensures high collection efficiency. A suitable tapered element oscillating microbalance is described in commonly assigned U.S. Pat. No. 4,391,338, with further background information provided in U.S. Pat. No. 3,926,271. The teachings of these two patents, in their entirety, are incorporated herein by reference.

In the preferred microbalance, a tapered hollow element is made to oscillate in a clamped-free mode. A filter is mounted at a free end of the element and serves to collect particulate matter from the particle laden gas stream. When this stream passes through the filter and then through the hollow element, the frequency of oscillation of the hollow element varies with mass loading of the filter and is readily convertible to a mass reading. For purposes of the present invention, changes in frequency of oscillation of the oscillating element with respect to each measurement time period is advantageously converted to a mass rate (i.e. change in mass with respect to the measured time interval) to determine a corrected mass concentration, as more fully described hereinafter.

Although a tapered hollow element oscillating microbalance is preferred, oscillating elements of other forms or configurations, e.g. non-tapered, tuning fork or U-shaped, or one operating in another mode, e.g. clamped-clamped mode, or a collector made to oscillate in a direction generally perpendicular to a plane of the collector, or an impaction plate or other particle collector, may also be employed as the mass detector.

In operation, with the particle remover 14 off, the mass detector 16 will measure an effective mass, $M_{Aeff}$, due to frequency changes resulting from mass changes and instrument effects, over a time period, $\Delta t$:

$$M_{Aeff} = M_p + M_{pv} + \alpha M_G + \beta \Delta T + \gamma \Delta P \qquad (1)$$

where:
$M_p$=non-volatile component of particulate mass
$M_{pv}$=volatile component of particulate mass
$\alpha M_G$=gaseous mass gain or loss due to filter adsorption/desorption and other filter artifacts, and deposited material volatilization
$\beta \Delta T$=effective mass equivalent of frequency change due to temperature change, $\Delta T$, during time interval, $\Delta t$
$\gamma \Delta P$=effective mass equivalent of frequency change due to pressure change, 66 P, during time interval, $\Delta t$.

During a consecutive time interval, $\Delta t$, particle remover 14 is on, i.e. $M_p$ and $M_{pv}$ are removed from the gas stream and are not measured on mass detector 16, and:

$$M_{Beff} = \alpha M_G + \beta \Delta T + \gamma \Delta P \qquad (2)$$

Therefore:

$$M_{Aeff} - M_{Beff} = M_p + M_{pv} + \alpha M_G + \beta \Delta T + \gamma \Delta P - (\alpha M_G + \beta \Delta T + \gamma \Delta P) = M_p + M_{pv} \qquad (3)$$

These measurement time intervals $\Delta t$ are kept relatively short in comparison to the rate of change in particulate concentration and in other mass measurement affecting parameters, e.g. temperature and pressure, so that vaporization effects, the adsorption/desorption effects of gases or vapors in the gas stream, other filter artifacts, and temperature and pressure change effects remain comparable during the 2 successive measurement time periods, allowing an accurate subtraction.

The mass detector 16 when the particle remover 14 is not activated during a particular measurement time period, provides a mass reading, i.e. mass gain, representative of the mass of particulate matter collected during that time period. An effective measure of the mass lost due to volatilization during that same time period is provided by the mass detector during a consecutive measurement time period during which the mass detector 16 is engaged by the particle free (particle remover activated) gas stream. Subtracting the two mass readings, effectively adds the lost mass to the measured mass gain to provide a corrected and accurate measure of the particulate matter mass.

In practice, the measurements can be based on mass rates utilizing the switching time as a convenient time basis. By subtracting mass rates, as opposed to total mass measurements, any slight calibration error in the measurement system will produce only a comparable final error in the results. If mass were strictly used, this error could accumulate to unacceptable levels as monitoring time continues.

Figure 2:
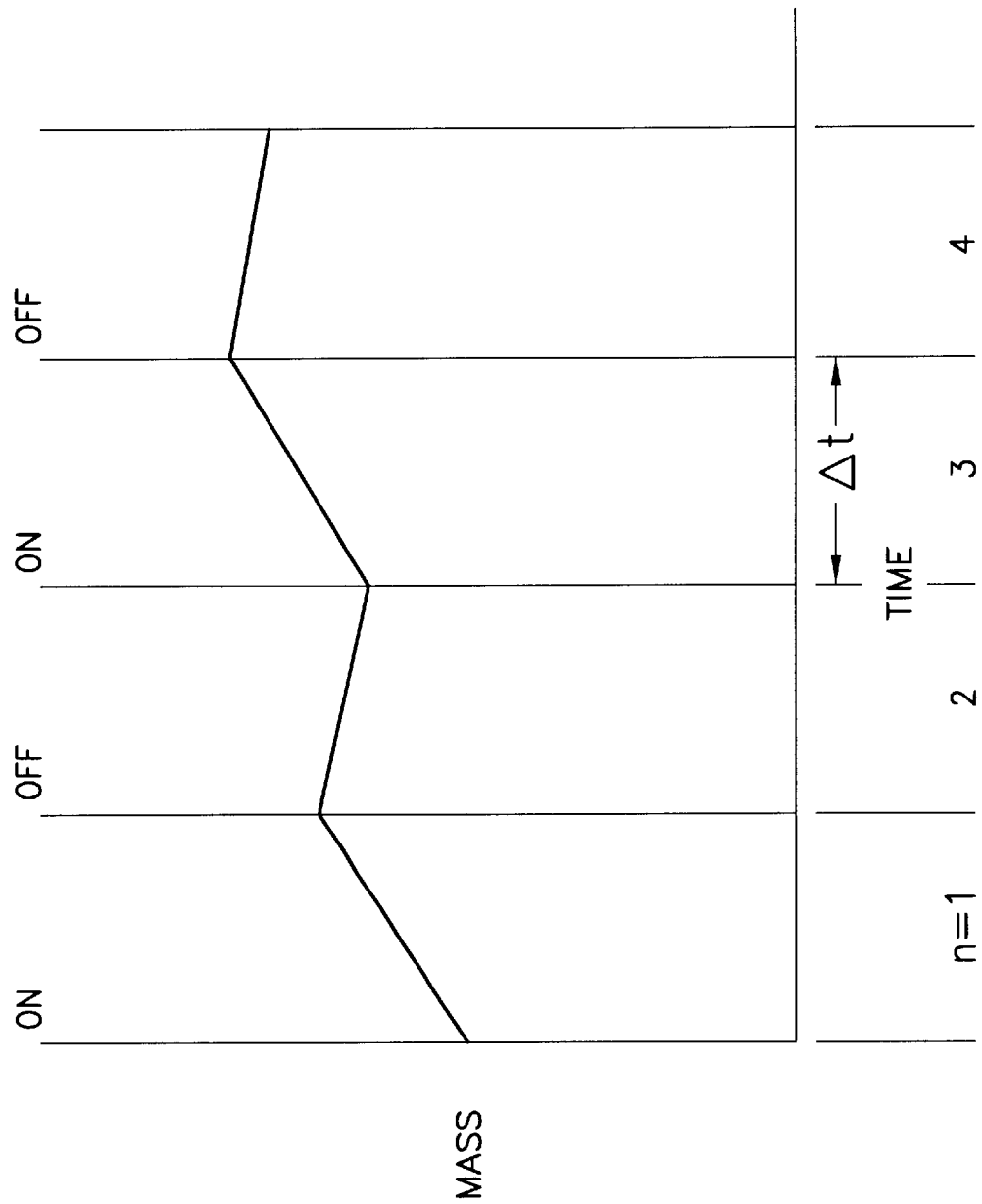
FIG. 2 is a graphical depiction useful in understanding how corrected mass concentration can be derived from mass rate readings of the detector of the differential particulate mass measuring apparatus of the present invention.

FIG. 2 depicts an example of how mass might vary over four successive measurement time periods as measured by the detector 16 of the instrument of the present invention. A corrected mass concentration can be calculated in accordance with the following relationships:

$$(-1)^{n+1}(\Delta m_B/\Delta t)_n + (-1)^n(\Delta m_A/\Delta t)_n = (\Delta m/\Delta t)_n \qquad (4)$$

and $$(MC)_n = (\Delta m/\Delta t)_n (1/F) = \frac{\Delta m}{\Delta V_n} \qquad (5)$$

where:
$\Delta t$ represents a time interval of a measurement time period,
n represents a measurement time period index, for even n's, the particle free gas stream engages the mass detector, and for odd n's, the particle laden gas stream engages the mass detector,
$\Delta m_A/\Delta t$ represents mass rate measured by the mass detector during an odd n measurement time period,
$\Delta m_B/\Delta t$ represents mass rate measured by the mass detector during an even n measurement time period,
$\Delta m/\Delta t$ represents corrected mass rate,
$\Delta V_n$ represents the volume of gas sampled during measurement period n,
F represents flow, and
MC represents corrected mass concentration.

In equation (4) above, the indexing to (−1) effectuates a subtraction of the readings.

Figure 3:
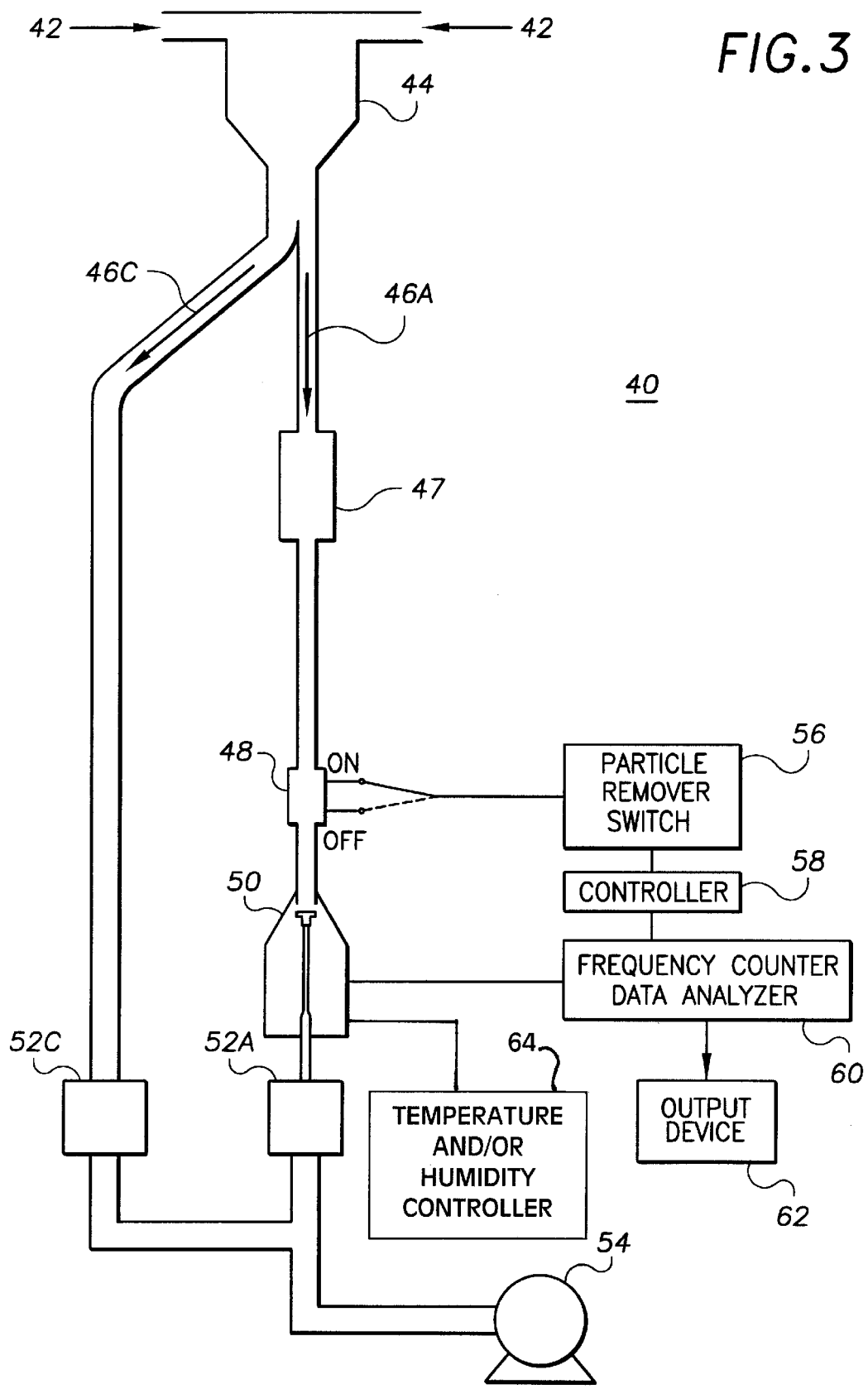
FIG. 3 illustrates an alternate embodiment of the apparatus of the present invention.

FIG. 3 illustrates an alternate embodiment of the differential particulate mass measurement apparatus of the present invention. In measurement instrument 40, a particle laden gas stream 42 is drawn in through a particle size selective inlet 44, of conventional construction, and then is split into two streams 46A, and 46C. Particle laden gas stream 46A flows through an optional dryer or dehumidifier 47 (e.g. a Perma Pure PD™-Series gas dryer of Nafion® construction available from Perma Pure Inc. of Toms River, N.J.), then through a selectively activatable particle remover (e.g. electrostatic precipitator) 48, and then engages mass detector (e.g. tapered element oscillating microbalance) 50. Dryer 47 advantageously serves to reduce, control, or eliminate water vapor in gas stream 46A. Stream 46C represents a by-pass flow to allow proper flow rate through inlet 44. Flow controllers 52A and 52C serve to maintain a desired constant flow rate in stream 46A and at mass detector 50. For example, if the flow rate out of inlet 44 is 16.7 l/min, flow controller 52A can maintain a flow rate of 2.0 l/min in stream 46A, while flow controller 52C maintains a flow rate of 14.7 l/min in stream 46C. A common vacuum pump 54 working in conjunction with the flow controllers establishes the desired flow. A particle remover switch 56 activates particle remover 48 for alternate successive measurement time periods as directed by controller 58. Controller 58 which can readily be implemented by a microcomputer or other known processor, also controls a frequency counter data analyzer 60 which receives frequency readings from mass detector 50 and, in known fashion, transforms such frequency readings into mass readings. From these mass readings, a measure of the mass and/or concentration of particulate matter in the particle laden gas stream 42 is determined, as earlier described, by analyzer 60, and then provided to output device 62. As will be readily apparent to those skilled in this art, switch 56, controller 58, data analyzer 60, output device 62 and the other components of this apparatus can take many different forms.

The operation of instrument 40 is identical to that described earlier for instrument 10.

Although preferred embodiments have been described and depicted herein, it will be readily apparent to those skilled in the art that various modifications, substitutions, additions and the like can be made without departing from the spirit of the invention. For example, switching of the particle free gas stream and the particle laden gas stream with respect to the mass detector can be accomplished by various alternative approaches including mechanically switching, e.g. with a valve, between a particle laden and a particle free gas stream, or mechanically switching the location of the detector. Rather than an electrostatic precipitator, a filter, e.g. a low pressure drop electrolet filter or other particle remover can be employed to create the particle free gas stream. Depending upon the intended application and operating conditions, a denuder to reduce gaseous component(s), temperature and/or humidity control equipment 64 (such as that taught in copending, commonly assigned U.S. Ser. No. 09/014,252, now U.S. Pat. No. 6,151,953 incorporated, in full, herein by reference), and other gas stream and/or particulate matter conditioning apparatus may also be used with the differential particulate mass monitor. The readings provided by the mass detector may comprise frequency, mass, mass rate, mass concentration or other parameter(s).

What is claimed is:

1. Apparatus for measuring the mass of particulate matter in a particle laden gas stream, comprising:
    a mass detector including a particulate matter collector;
    first means upstream of said mass detector for providing a particle free gas stream otherwise substantially identical to said particle laden gas stream;
    switching means for causing said particle laden gas stream and said particle free gas stream to alternately engage said mass detector during successive measurement time periods; and
    second means for determining a difference between a first reading provided by the mass detector for a current measurement time period and a second reading provided by the mass detector for a successive measurement time period, which difference intrinsically corrects for volatilization losses of collected particulate matter from said collector occurring during the current measurement time period, and for determining from said difference a measure of the mass or concentration of particulate matter in the particle laden gas stream.

2. The apparatus of claim 1 wherein said first means comprises particle removal means for removing substantially all particulate matter from said particle laden gas stream to provide said particle free gas stream.

3. The apparatus of claim 2 wherein said particle removal means removes said particulate matter from said particle laden gas stream while maintaining gas stream temperature, pressure and flow rate substantially the same.

4. The apparatus of claim 3 wherein said particle removal means comprises an electrostatic precipitator.

5. The apparatus of claim 4 wherein said electrostatic precipitator operates in a low current, positive corona mode.

6. The apparatus of claim 1 further comprising a dryer for reducing water vapor in the particle laden gas stream and in the particle free gas stream.

7. The apparatus of claim 1 wherein a reading provided by the mass detector comprises a mass rate rating.

8. The apparatus of claim 1 wherein the mass detector comprises an oscillating element microbalance.

9. The apparatus of claim 1, wherein the switching means causes:
    (a) the particle laden gas stream to engage the mass detector during each of odd numbered ones of the successive measurement time periods, and
    (b) said particle free gas stream to engage the mass detector during each of even numbered ones of the successive measurement time periods; and
    wherein, when the detector is engaged by the particle laden gas stream, the detector measures mass gain, and, when the detector is engaged by the particle free gas stream, the detector measures mass loss; and
    wherein the second means effectively adds the measured mass loss to the measured mass gain to determine the measure of the mass or concentration of the particulate matter in the particle laden gas stream.

10. The apparatus of claim 9 wherein the mass lost represents mass of volatile component of said particulate matter.

11. The apparatus of claim 10 wherein each of said successive measurement time periods lasts for no more than about fifteen minutes.

12. The apparatus of claim 10 wherein each of said successive measurement time periods lasts for no more than about a minute.

13. The apparatus of claim 1 wherein said measure of the mass of particulate matter in the particle laden gas stream comprises a corrected mass concentration determined in accordance with the following relationships:

$$(-1)^{n+1}(\Delta m_B/\Delta t)_n + (-1)^n(\Delta m_A/\Delta t)_n = (\Delta m/\Delta t)_n$$

and $$(MC)_n = (\Delta m/\Delta t)_n (1/F) = \frac{\Delta m}{\Delta V_n}$$

where:
    $\Delta t$ represents a time interval of a measurement time period, n represents a measurement time period index, for even n's, the particle free gas stream engages the mass detector, and for odd n's, the particle laden gas stream engages the mass detector, $\Delta m_A/\Delta t$ represents mass rate measured by the mass detector during an odd n measurement time period, $\Delta m_B/\Delta t$ represents mass rate measured by the mass detector during an even n measurement time period, $\Delta m/\Delta t$ represents corrected mass rate, $\Delta V n$ represents the volume of gas sampled during measurement period n, F represents flow, and MC represents corrected mass concentration.

14. The apparatus of claim 1 wherein said first means comprises a filter.

15. The apparatus of claim 14 further including at least one of a temperature controller and a humidity controller.

16. The apparatus of claim 14 including both a temperature controller and a humidity controller.

17. Apparatus for measuring the mass of particulate matter, including volatile components thereof, in a particle laden gas stream, comprising:

a mass detector including a particulate matter collector;

means for directing said stream to continually engage said mass detector;

particle removal means upstream of said mass detector for removing substantially all particulate matter from said stream when said particle removal means is activated; and control means for activating said particle removal means for alternate successive measurement time periods; and second means for determining a difference between a first reading provided by the mass detector for a current measurement time period and a second reading provided by the mass detector for a successive measurement time period, which difference intrinsically corrects for volatilization losses of collected particulate matter from said collector occurring during the current measurement time period, and for determining from said difference a measure of the mass or concentration of particulate matter in the particle laden gas stream.

18. The apparatus of claim 17 wherein said particle removal means comprises an electrostatic precipitator.

* * * * *

UNITED STATES PATENT AND TRADEMARK OFFICE
CERTIFICATE OF CORRECTION

PATENT NO.   : 6,502,450 B1
DATED        : January 7, 2003
INVENTOR(S)  : Patashnick et al.

It is certified that error appears in the above-identified patent and that said Letters Patent is hereby corrected as shown below:

<u>Title page,</u>
Item [73], Assignee: delete "Patashnik" and insert -- Patashnick --.

Signed and Sealed this

Twenty-fifth Day of March, 2003

JAMES E. ROGAN
*Director of the United States Patent and Trademark Office*